US008065180B2

(12) United States Patent
Hufford et al.

(10) Patent No.: US 8,065,180 B2
(45) Date of Patent: Nov. 22, 2011

(54) SYSTEM FOR CLINICAL TRIAL SUBJECT COMPLIANCE

(75) Inventors: Michael Hufford, San Diego, CA (US); David Peterson, Scotts Valley, CA (US); Jean A. Paty, Pittsburgh, PA (US); Saul Shiffman, Pittsburgh, PA (US)

(73) Assignee: invivodata®, Inc., Pittsburgh, PA (US)

( * ) Notice: Subject to any disclaimer, the term of this patent is extended or adjusted under 35 U.S.C. 154(b) by 1347 days.

(21) Appl. No.: 09/825,533

(22) Filed: Apr. 2, 2001

(65) Prior Publication Data
US 2002/0143563 A1 Oct. 3, 2002

(51) Int. Cl.
*G06Q 10/00* (2006.01)
(52) U.S. Cl. .............................................. 705/11; 705/3
(58) Field of Classification Search .................. 705/2, 3, 705/4; 365/230.03; 600/529
See application file for complete search history.

(56) References Cited

U.S. PATENT DOCUMENTS

| | | | |
|---|---|---|---|
| D247,251 S | 2/1978 | Napoli | D24/17 |
| 4,262,632 A | 4/1981 | Hanton et al. | 119/1 |
| 4,353,375 A | 10/1982 | Colburn et al. | 128/782 |
| 4,367,752 A | 1/1983 | Jimenez et al. | 128/689 |
| 4,543,955 A | 10/1985 | Schroeppel | 128/635 |
| 4,566,461 A | 1/1986 | Lubell et al. | 128/668 |
| 4,592,018 A | 5/1986 | Wiegman | 365/63 |
| 4,686,624 A | 8/1987 | Blum et al. | 364/415 |
| 4,803,625 A | 2/1989 | Fu et al. | 364/413.03 |
| 4,844,076 A | 7/1989 | Lesho et al. | 128/631 |
| 4,883,063 A | 11/1989 | Bernard et al. | 128/670 |
| 4,909,260 A | 3/1990 | Salem et al. | 128/721 |
| 4,966,154 A | 10/1990 | Cooper et al. | 128/671 |
| 4,974,601 A | 12/1990 | Tranjan et al. | 128/696 |
| 4,975,842 A | 12/1990 | Darrow et al. | 364/413.02 |
| 4,987,897 A | 1/1991 | Funke | 128/419 PG |
| 5,002,064 A | 3/1991 | Allain et al. | 128/710 |
| 5,063,937 A | 11/1991 | Ezenwa et al. | 128/723 |
| 5,078,134 A | 1/1992 | Heilman et al. | 128/421 |
| 5,111,818 A | 5/1992 | Suzuki et al. | 128/644 |
| 5,113,859 A | 5/1992 | Funke | 128/419 PG |
| 5,128,552 A | 7/1992 | Fang et al. | 307/66 |

(Continued)

FOREIGN PATENT DOCUMENTS
EP 299667 A1 1/1989
(Continued)

OTHER PUBLICATIONS

Kiuchi, T., Ohashi, Y., Konishi, M., Bandai, Y., Kosuge, T., and Kakizoe, T. "A World Wide Web-based User Interface for a Data Management System for Use in Multi-institutional clinical Trials—Development and Experimental Operation of an Automated Patient Registration and Random Allocation System." *Controlled Clinical Trials*, vol. 17, pp. 476-493 (1996). Elsevier Sciences, Inc., New York, NY.*

(Continued)

*Primary Examiner* — Lindsay M. Maguire
(74) *Attorney, Agent, or Firm* — Wilson Sonsini Goodrich & Rosati

(57) ABSTRACT

The present invention is designed to develop research protocols for clinical trials. The invention also can track and enhance subject compliance with a research protocol. The invention further provides evaluability data related to subject performance in the clinical trial. According to an alternative embodiment of the invention, a portable electronic device is used to query and collect data from the subject.

34 Claims, 5 Drawing Sheets

U.S. PATENT DOCUMENTS

| | | | | |
|---|---|---|---|---|
| 5,131,390 A | 7/1992 | Sakaguchi et al. | | 128/632 |
| 5,137,345 A | 8/1992 | Waldorf et al. | | 351/206 |
| 5,181,519 A | 1/1993 | Bible | | 128/704 |
| 5,197,489 A | 3/1993 | Conlan | | 128/782 |
| 5,199,439 A | 4/1993 | Zimmerman et al. | | 128/670 |
| 5,213,106 A | 5/1993 | Lerner | | 128/696 |
| 5,213,555 A | 5/1993 | Hood et al. | | 482/57 |
| 5,218,969 A | 6/1993 | Bredesen et al. | | 128/710 |
| 5,222,503 A | 6/1993 | Ives et al. | | 128/731 |
| 5,226,424 A | 7/1993 | Bible | | 128/696 |
| 5,226,539 A | 7/1993 | Cheng | | 206/534 |
| 5,228,450 A | 7/1993 | Sellers | | 128/711 |
| 5,253,654 A | 10/1993 | Thomas et al. | | 128/779 |
| 5,261,412 A | 11/1993 | Butterfield et al. | | 128/672 |
| 5,271,405 A | 12/1993 | Boyer et al. | | 128/672 |
| 5,275,159 A | 1/1994 | Griebel | | 128/633 |
| 5,280,429 A | 1/1994 | Withers | | 364/413.15 |
| 5,289,824 A | 3/1994 | Mills et al. | | 128/696 |
| 5,307,263 A | 4/1994 | Brown | | 364/413.09 |
| 5,412,769 A | 5/1995 | Maruoka et al. | | |
| 5,447,164 A | 9/1995 | Shaya et al. | | 128/710 |
| 5,454,376 A | 10/1995 | Stephens et al. | | 128/721 |
| 5,583,831 A | 12/1996 | Churchill et al. | | 368/10 |
| 5,596,994 A | 1/1997 | Bro | | 128/732 |
| 5,671,734 A * | 9/1997 | Pugh | | 600/301 |
| 5,672,154 A | 9/1997 | Sillén et al. | | 604/50 |
| 5,704,366 A | 1/1998 | Tacklind et al. | | 128/716 |
| 5,710,551 A | 1/1998 | Ridgeway | | 340/870.09 |
| 5,732,709 A | 3/1998 | Tacklind et al. | | 128/726 |
| 5,778,882 A | 7/1998 | Raymond et al. | | 128/700 |
| 5,832,448 A | 11/1998 | Brown | | 705/2 |
| 5,960,403 A | 9/1999 | Brown | | 705/2 |
| 5,963,136 A | 10/1999 | O'Brien | | 340/573.1 |
| 5,980,429 A * | 11/1999 | Nashner | | 482/8 |
| 6,039,688 A | 3/2000 | Douglas et al. | | 600/300 |
| 6,051,029 A | 4/2000 | Paterson et al. | | |
| 6,063,028 A | 5/2000 | Luciano | | |
| 6,075,755 A | 6/2000 | Zarchan | | 368/10 |
| 6,095,985 A | 8/2000 | Raymond et al. | | 600/513 |
| 6,151,586 A | 11/2000 | Brown | | 705/14 |
| 6,167,362 A | 12/2000 | Brown et al. | | 703/11 |
| 6,171,237 B1 * | 1/2001 | Avitall et al. | | 600/300 |
| 6,317,731 B1 | 11/2001 | Luciano | | |
| 6,381,577 B1 | 4/2002 | Brown | | 705/2 |
| 6,514,200 B1 * | 2/2003 | Khouri | | 600/300 |
| 6,663,846 B1 * | 12/2003 | McCombs et al. | | 424/9.2 |
| 6,687,190 B2 * | 2/2004 | Momich et al. | | 368/10 |
| 6,827,670 B1 * | 12/2004 | Stark et al. | | 482/9 |
| 6,865,519 B2 | 3/2005 | Lampert et al. | | |
| 6,879,970 B2 | 4/2005 | Shiffman et al. | | |
| 6,895,405 B1 | 5/2005 | Choi et al. | | |
| 6,996,560 B1 | 2/2006 | Choi et al. | | |
| 7,058,517 B1 * | 6/2006 | Denton et al. | | 702/20 |
| 7,185,065 B1 | 2/2007 | Holtzman et al. | | |
| 7,251,609 B1 * | 7/2007 | McAlindon et al. | | 705/3 |
| 7,873,589 B2 | 1/2011 | Shiffman et al. | | |
| 2001/0044408 A1 * | 11/2001 | Reitberg | | 514/1 |
| 2002/0013516 A1 * | 1/2002 | Freyre et al. | | 600/300 |
| 2002/0019748 A1 | 2/2002 | Brown | | 705/2 |
| 2002/0042726 A1 | 4/2002 | Mayaud | | 705/2 |
| 2002/0052858 A1 | 5/2002 | Goldman et al. | | |
| 2002/0064095 A1 | 5/2002 | Momich et al. | | 368/10 |
| 2002/0099570 A1 | 7/2002 | Knight | | |
| 2002/0120471 A1 * | 8/2002 | Drazen | | 705/3 |
| 2002/0143595 A1 | 10/2002 | Frank et al. | | |
| 2003/0036683 A1 * | 2/2003 | Kehr et al. | | 600/300 |
| 2003/0178031 A1 * | 9/2003 | Du Pen et al. | | 128/898 |
| 2003/0194704 A1 | 10/2003 | Penn et al. | | |
| 2004/0024639 A1 | 2/2004 | Goldman | | |
| 2004/0122701 A1 * | 6/2004 | Dahlin et al. | | 705/2 |
| 2005/0154676 A1 | 7/2005 | Ronning et al. | | |
| 2005/0165626 A1 * | 7/2005 | Karpf | | 705/3 |
| 2008/0052259 A1 | 2/2008 | Shiffman et al. | | |
| 2011/0082827 A1 | 4/2011 | Shiffman et al. | | |

FOREIGN PATENT DOCUMENTS

| | | | |
|---|---|---|---|
| EP | 1 034 734 | A1 | 9/2000 |
| FR | 2686497 | A1 | 7/1993 |
| WO | WO 88/02237 | A1 | 4/1988 |
| WO | WO 89/05116 | A1 | 6/1989 |
| WO | WO 94/01040 | A1 | 1/1994 |
| WO | WO 94/01049 | A1 | 1/1994 |
| WO | WO 94/13198 | A1 | 6/1994 |
| WO | WO 94/24929 | A1 | 11/1994 |
| WO | WO 96/13790 | A1 | 5/1996 |
| WO | WO 98/38909 | A1 | 9/1998 |
| WO | WO 99/27483 | A1 | 6/1999 |
| WO | WO 99/38052 | A1 | 7/1999 |
| WO | WO 00/15103 | A1 | 3/2000 |
| WO | WO 00/69331 | A1 | 11/2000 |
| WO | WO 00/75748 | A2 | 12/2000 |
| WO | WO 01/06433 | A1 | 1/2001 |
| WO | WO 01/09701 | A1 | 2/2001 |
| WO | WO 01/26020 | A1 | 4/2001 |
| WO | WO 01/26021 | A1 | 4/2001 |
| WO | WO 01/34024 | A1 | 5/2001 |
| WO | WO 01/74229 | A2 | 10/2001 |
| WO | WO 02/19247 | A2 | 3/2002 |
| WO | WO 2006/009331 | A1 | 1/2006 |

OTHER PUBLICATIONS

Smith, G., "Statistical Reasoning." Third edition. Ch. 15, pp. 619-667. Allyn and Bacon (a Division of Simon and Schuster, Inc.), Needham Heights, MA. 1991.*

Collins RL, et al. "Ecological momentary assessment in a behavioral drinking moderation training program" *Exp. Clin. Psychopharmacol.* Aug. 1998;6(3):306-15.

Cramer, JA et al. "How often is medication taken as prescribed?" *JAMA* 1989;261:3273-3277.

Eich, E, et al. "Memory for Pain: Relation between Past and Present Pain Intensity" *Pain* 1985;23:375-379.

Friedman, WJ "Memory for the Time of Past Events" *Psychological Bulletin* 1993;113(1):44-66.

Gorin AA, et al. "Recall Biases and Cognitive Errors in Retrospective Self-Reports: A Call for Momentary Assessments" *Handbook of Heath Psychology.* Lawrence Erlbaum Assoc.:Mahwah, NJ. 2001;pp. 405-413.

Greeno CG, et al. "Binge antecedents in obese women with and without binge eating disorder" *J. Consult. Clin. Psychol.* Feb. 2000;68(1):95-102.

Hyland, ME, et al. "Diary keeping in asthma: comparison of written and electronic methods" *BMJ* Feb. 20, 1993;306(6876):487-489.

Karmack TW, et al. "The effects of psychosocial influences on ambulatory blood pressure: contrasting different measurement and data analytic strategies" 37th Annual Meeting of the Society for Psychophysical Research, North Falmouth, Massachusetts, USA, Oct. 15-19, 1997. *Psychophysiology* 1997;34 (Suppl. 1):S6-S7.

Kamarck TW, et al. "Effects of task strain, social conflict, and emotional activation on ambulatory cardiovascular activity: daily life consequences of recurring stress in a multiethnic adult sample" *Health Psychol.* Jan. 1998;17(1):17-29.

Kamarck TW, et al. "Emotional Support Modrates the Acute Pressor Effects of Stress During Daily Life" Abstracts of Papers for 1999 Annual Meeting: Paper Session: Cardiovascular Activity in Relation to Stress Psychology and Neurobiology. *Psychosomatic Medicine* 1999;6(1):112 (abstract).

Kamarck TW, et al. "The Diary of Ambulatory Behavioral States: A new Approach to the Assessment of Psychosocial Influences on Ambulatory Cardiovascular Activity" *Technology and Methods in Behavioral Medicine* (D.S. Krantz and A. Baum, eds.) Lawrence Erlbaum Associates: Mahwah, NJ. 1998; Chapter 9:163-193.

O'Connell KA, et al. "Overcoming the Urge to Smoke: The Strategies of Long-Term Abstainers and Late Relapsers" *Psychology of Addictive Behavior* 1991;5(1):1-8.

O'Connell KA, et al. "Coping in real time: using Ecological Momentary Assessment techniques to assess coping with the urge to smoke" *Res. Nurs. Health.* Dec. 1998;21(6):487-97.

O'Connell KA, et al. "Symptom beliefs and actual blood glucose in type II diabetes" *Res. Nurs. Health.* Jun. 1990;13(3):145-51.

O'Connell KA, et al. "Reversal theory and smoking: a state-based approach to ex-smokers' highly tempting situations" *J. Consult. Clin. Psychol.* Aug. 1990;58(4):489-94.

O'Connell KA "Why rational people do irrational things. The theory of psychological reversals" *J. Psychosoc. Nurs. Ment. Health Serv.* Jan. 1991;29(1):11-4.

Paty, J, et at. "The importance of assessing base rates for clinical studes: an example of stimulus control of smoking" *The Experience of Psychopathology: Investigating Mental Disorders in their Natural Settings* (DeVries, Marten W. ed.) Cambridge: Cambridge University Press. 1992; pp. 347-352.

Penner, LA, et al. "Individual Differences in Intraperson Variability in Mood" *Journal of Personality and Social Psychology* 1994;6694):712-721.

Potocky M, et al. "State-outcome consistency in smoking relapse crises: a reversal theory approach" *J. Consult. Clin. Psychol.* Apr. 1991;59(2):351-3.

Raynor, DA et al. "The effects of social influence on cardiovascular responsiveness in the natural environment" 37th Annual Meeting of the Society for Psychophysical Research, N. Falmouth, Massachusetts, USA, Oct. 15-19, 1997. *Psychophysiology* 1997;34 (Suppl. 1):S73.

Ross, M "Relation of Implicit Theories to the Construction of Personal Histories" *Psychological Review* 1989;96(2):341-357.

Schwartz JE, et al. "Does trait coping exist? A momentary assessment approach to the evaluation of traits" *J. Pers. Soc. Psychol.* Aug. 1999;77(2):360-9.

Schwartz JE, et al. "Strategies for analyzing ecological momentary assessment data" *Health Psychol.* Jan. 1998;17(1):6-16.

Shiffman S. "Real-Time Self-Report of Momentary States in the Natural Environment: Computerized Ecological Momentary Assessment" *The Science of Self-Report: Implicates for Research and Practice* (A. Stone, et al. eds.) Mahwah, NJ: Lawrence Erlbaum Associates. 1989; Chapter 16: 277-296.

Shiffman, Saul "Assessing Smoking Patterns and Motives" *Journal of Consulting and Clinical Psychology* 1993;61(5):732-742.

Shiffman S, et al. "Drinking and Smoking: A Field Study of their Association" *Annals of Behavioral Medicine* 1994; 16(3):203-209.

Shiffman S, et al. "Nicotine withdrawal in chippers and regular smokers: subjective and cognitive effects" *Health Psychol.* Jul. 1995;14(4):301-9.

Shiffman S, et al. "First lapses to smoking: within-subjects analysis of real-time reports" *J. Consult. Clin. Psychol.* Apr. 1996;64(2):366-79.

Shiffman S, et al. "Progression from a smoking lapse to relapse: prediction from abstinence violation effects, nicotine dependence, and lapse characteristics" *J. Consult. Clin. Psychol.* Oct. 1996;64(5):993-1002.

Shiffman S, et al. "Temptations to smoke after quitting: a comparison of lapsers and maintainers" *Health Psychol.* Nov. 1996;15(6):455-61.

Shiffman S, et al. "A day at a time: predicting smoking lapse from daily urge" *J. Abnorm. Psychol.* Feb. 1997;106(1):104-16.

Shiffman S, et al. "Remember that? A comparison of real-time versus retrospective recall of smoking lapses" *J. Consult. Clin. Psychol.* Apr. 1997;65(2):292-300.

Shiffman S, et al. "Individual differences in the context of smoking lapse episodes" *Addict. Behav.* Nov.-Dec. 1997;22(6):797-811.

Shiffman S, et al. "The Abstinence Violation Effect Following Smoking Lapses and Temptations" *Cognitive Therapy and Research* 1997; 21(5):497-523.

Shiffman S, et al. "The effect of bupropion on nicotine craving and withdrawal" *Psychopharmacology (Berl)* Jan. 2000;148(1):33-40.

Shiffman S, et al. "Dynamic effects of self-efficacy on smoking lapse and relapse" *Health Psychol.* Jul. 2000;19(4):315-23.

Shiffman S, et al. "Comparative efficacy of 24-hour and 16-hour transdermal nicotine patches for relief of morning craving" *Addiction* Aug. 2000;95(8):1185-95.

Stone, AA, et al. "Ecological Momentary Assessment (EMA) in Behavioral Medicine" *Annals of Behavioral Medicine* 1994;16(3):199-202.

Stone, AA, et al. "A comparison of coping assessed by ecological momentary assessment and retrospective recall" *J. Pers. Soc. Psychol.* Jun. 1998;74(6):1670-80.

Stone, AA, et al. "Ecological Momentary Assessment" *Well-being: The foundations of Hedonic psychology.* Kahneman, Daniel et al. (eds.). Russell Sage Foundation: New York, NY. 1999; pp. 26-39.

Stone, AA, et al. "Does the peak-end phenomenon observed in laboratory pain studies apply to real-world pain in rheumatoid arthritics?" *The Journal of Pain* Fall 2000;1(3):212-217.

Straka, RJ, et al. "Patient self-reporting of compliance does not correspond with electronic monitoring: an evaluation using isosorbide dinitrate as a model drug" *Pharmacotherapy* Jan.-Feb. 1997;17(1):126-32.

Wiesspeiner, G, et al. "Multichannel Ambulatory Monitoring of Circulation Related Biosignals" *Proceedings. Computers in Cardiology*, Sep. 23-26, 1991, Venice, Italy. IEEE Comput. Soc. Press, Los Alamitos, CA, USA 1991: p. 457-60.

Powell, JH "Handhelds aid doctors" Retrieved from the Internet, www.bostonherald.com/business/technology/palm07032000.htm Jul. 3, 2000.

Salford Systems "CART® for Windows User's Guide. A Salford Systems Implementation of the Original CART Program" 1999:i-v, 1-90, Index.

Tomkies, KK "Taking a New Tack on Clinical Trial Data Collecion: New Internet-based software aims to improve data integrity, helping speed data transmission in the process" Retrieved from the Internet www.office.com/global/0,,53-17789,FF.html May 28, 2000.

Dahlstrom, et al. Patient Computers to Enhance Compliance with Completing Questionnaires: a Challenge for the 1990s. Patient Compliance in Medical Practice and Clinical Trials (ed. By J.A. Cramer and B. Spilker). New York: Raven Press. 1991: 233-40.

Lussier, et al. PureMD: a Computerize Patient Record Software for Direct Data Entry by Physicians: Using a Keyboardless Pen-Based Portable Computer. American Medical Informatics Association, McGraw Hill. 1992; 261-264.

Tattersall, et al. The Use of a Hand-held Computer to Record Clinical Trial Data in General Practice: a Pilot Study. The Journal of International Medical Research. 1989; 17:185-89.

Taylor, et al. The use of a real-time computer diary for data acquisition and processing. Behav. Res. Ther. 1990; (28)1:93-97.

Totterdell, et al. In situ repeated measures of affect and cognitive performance facilitated by use of a hand-held computer. Behavior Research Methods, Instruments and Computers. 1992; 24(4):545-53.

Zimmet, et al. Computer-Based Patient Monitoring Systems: Use in Research and Clinical Practice. Diabetes Care. Nov. /Dec. 1988; (11) Supp. 1:62-6.

Invivodata postcard mail item. 2001.

Invivodata company newsletter dated 4th quarter 2001.

Engfer, et al. Technology in service of science. Invivodata, Inc. Jan. 30, 2001 (9 pages).

Hufford, et al. Quality of life and patient experience research. Invivodata, Inc. Jan. 30, 2001 (10 pages).

Shiffman, et al. The scientific principles underlying patient experience research: Ecological momentary assessment. Invivodata, Inc. Jan. 30, 2001 (8 pages).

Shiffman, et al. Methods of measuring patient experience: Paper versus electronic patient diaries. Invivodata, Inc. Jan. 30, 2001 (9 pages).

Shiffman, et al. Patient experience: A growing focus in clinical trials. Invivodata, Inc. Jan. 30, 2001 (8 pages).

Shiffman, et al. Subject experience diaries in clinical research, Part 1: The patient experience movement; Part 2: Ecological momentary assessment. Applied Clinical Trials. Feb. & Mar. 2001 (12 pages).

Invivodata company press release dated Jun. 12, 2000: Invivodata Inc. provides science-based system to measure patient experience.

Invivodata company press release dated Jun. 12, 2000: Invivodata delivers new version of patient compliance monitoring.

Invivodata Announcement dated Jun. 13, 2000.

Invivodata company press release dated Oct. 12, 2000: Invivodata and RxCCI announce new partnership to improve quality and timeliness of clinical trials.

Invivodata company press release dated Nov. 28, 2000: Invivodata is first to guarantee patient compliance in clinical studies.

Invivodata. Application brief pain. Apr. 10, 2001 (2 pages).

Invivodata company press release dated Apr. 11, 2001: Invivodata leads way in clinical trial technology with wireless patient diary system.

Non-final office action mailed Feb. 19, 2009 in connection with U.S. Appl. No. 11/844,632.

Hufford, et al. Collecting reliable and valid real-time patient experience data. Drug Information Journal. 2001; 755-765.

Hufford, et al. Correspondence between paper and electronic visual analog scales among adult asthmatics. Invivodata. Nov. 9, 2001.

Invivodata, Inc. Insights. Third Issue. Jul. 2001.

Invivodata. Comparing electronic and paper diary data. Invivodata. Nov. 26, 2001.

Invivodata. Guaranteed patient compliance. Insight into patient behavior. Reduced study risks. Jul. 2001.

Invivodata. Innovations in Clinical Trial Technologies. Schedule for Seminar. 2001.

Invivodata. Prove it—your drug's performance beats the competition. Date?

* cited by examiner

SYSTEM FOR CLINICAL TRIAL SUBJECT COMPLIANCE

REFERENCE TO RELATED APPLICATIONS

The subject matter of this application relates to the patent application titled "Apparatus and Method for Prediction and Management of Subject Compliance in Clinical Research", U.S. patent application Ser. No. 09/825,534, now U.S. Pat. No. 6,879,970, and filed on even date herewith. The aforementioned application, and the references cited therein, are incorporated herein by reference.

FIELD OF THE INVENTION

The present invention relates to conducting clinical trials. Specifically, the invention relates to research protocol development, management of subject behavior and distribution of evaluability data.

BACKGROUND OF THE INVENTION

Noncompliance with research protocols can be especially problematic, potentially resulting in unusable trial data. Typically, subjects are given a paper-based diary and asked to make scheduled entries regarding their illness, medication effects, as well as other data entries recording events as they happen. Subjects must keep track of the time of day, where they are in the sequence of events for any given day, and the appropriate procedures they are to follow across days. Many subjects do not complete their diaries or complete their diaries long after the events that are to be logged. Eight studies have examined compliance rates of these paper diaries by covertly collecting data about the timeliness of entries. A dramatic difference between subjects' reported versus actual compliance was observed. Whereas the paper diaries appeared to indicate high rates of compliance (88%), the actual rates of compliance were significantly lower (54%).

Evaluation of subject compliance with research protocols is often performed by examining only one variable at a time. Such evaluation is not empirically derived by quantitative analysis of existing datasets. Instead the evaluation relies on the researcher's judgment and biases to determine whether and what type of corrective action is required. Furthermore, evaluation of subject compliance with clinical trial protocols has typically not taken into account the domain of the clinical trial or the characteristics of the subjects.

SUMMARY OF THE INVENTION

The goal of clinical trials is to collect valid, reliable data on one or more conditions within a clinical trial group of subjects. Subjects in clinical trials are assigned tasks related to treatment and data collection in accordance with a research protocol. The integrity of clinical trials rests upon subjects' faithful performance of these tasks. If subjects fail to comply with the protocol, the trial will fail to yield reliable, valid trial data or results. Thus, subject noncompliance in clinical trials is a significant risk and cost to the pharmaceutical industry. Accordingly, the creation of appropriate research protocol, management and enhancement of subject behavior and effective distribution of clinical trial data is of substantial value to clinical research.

The benefits of a system that can track and enhance subject compliance in a clinical trial include: reliable, valid data; increased statistical power, reduced clinical trial costs through smaller sample sizes; reduced time to complete the clinical trial; and, ultimately, reduced time to get a drug or medical device to market.

According to one embodiment of the invention, a method of protocol development for a clinical trial is provided. The method includes the steps of identifying a clinical trial target reflecting a goal of the clinical trial, determining desired evaluability data categories to be gathered pertaining to a participant in the clinical trial, wherein an evaluability data of at least one of the evaluability data categories is used to determine the desirability of retaining the participant in the trial or incorporating the participant in one or more of the trial results.

According to another embodiment of the invention, a method of determining preferred targets for subject compliance is provided, having the steps of providing at least one of the group of historical subject compliance data and historical protocol data and generating at least one preferred compliance threshold by quantitative analysis of at least one of the group of the historical subject compliance data and the historical protocol data.

Another embodiment of the invention provides a method of monitoring subject compliance and having the steps of providing historical subject compliance data, generating at least one algorithm reflective of the historical subject compliance by quantitative analysis of the historical subject compliance data and the historical protocol data, translating the at least one algorithm into at least one decision rule for analyzing subject compliance information, obtaining the subject compliance information, comparing the subject compliance information to the at least one decision rule to determine if corrective action is needed and prompting corrective action if the step of comparing indicates that corrective action is needed.

Another embodiment of the invention provides a method of determining subject compliance and having the steps of providing historical subject compliance data and historical protocol data, generating a spectrum of compliance representative of the historical subject compliance data not compliant with the historical protocol data by quantitative analysis of the historical subject compliance data and the historical protocol data, obtaining subject compliance information, comparing the spectrum of compliance to the subject compliance information to determine if corrective action is needed, and prompting corrective action if the step of comparing indicates that corrective action is needed.

Another embodiment of the invention provides a method of predicting subject noncompliance and having the steps of providing historical subject compliance data, generating at least one predictive algorithm for predicting subject noncompliance by quantitative analysis of the historical subject compliance data, translating the at least one predictive algorithm into at least one prediction rule, obtaining subject compliance information, comparing the subject compliance information to the at least one prediction rule to determine if action is needed, and prompting action if the step of comparing indicates that action is needed.

A further embodiment of the invention provides a method of enhancing subject compliance and having the steps of providing historical subject compliance data, generating at least one algorithm by quantitative analysis of the historical subject compliance data, translating at least one algorithm into at least one decision rule, obtaining subject compliance information and comparing the subject compliance information to the at least one decision rule to determine if affirmative action is warranted.

A further embodiment of the invention provides a compliance monitoring device for use in clinical trials, having a portable electronic device capable of displaying information and receiving and storing input from a user and an alarm electrically coupled to the portable electronic device and having varying alarm tones, wherein the varying alarm tones are emitted by the alarm if the user does not comply with a predetermined protocol for providing the input to the portable electronic device.

A further embodiment of the invention provides a compliance monitoring device for use in clinical trials, having a portable electronic device capable of displaying information and receiving and storing input from a user and an alarm electrically coupled to the portable electronic device and having a tactile alarm.

A further embodiment of the invention provides a compliance monitoring device for use in clinical trials, having a portable electronic device capable of displaying information and receiving and storing input from a participant in the clinical trial, wherein the portable electronic device examines the input and reviews the input for inconsistencies.

A further embodiment of the invention provides a compliance monitoring device for use in clinical trials, having a portable electronic device capable of displaying information and receiving and storing input from a participant in the clinical trial, wherein the portable electronic device increases an amount of prompting of the input from the participant upon an automated determination that the participant does not comply with a predetermined protocol for providing the input to the portable electronic device.

A further embodiment of the invention provides a compliance monitoring device for use in clinical trials, having a portable electronic device capable of displaying information and receiving and storing input from a participant in the clinical trial, wherein the portable electronic device decreases an amount of prompting of the input from the participant upon an automated determination that the participant has reported a predetermined number of events other than in response to the prompting by the portable electronic device.

A further embodiment of the invention provides a compliance monitoring device for use in clinical trials, having a portable electronic device capable of displaying information and receiving and storing input from a user, wherein the user is provided feedback based on the determination of whether the user has followed a predetermined protocol for providing the input to the portable electronic device.

A further embodiment of the invention provides a medium suitable for use in an electronic device and having instructions for execution on the electronic device, the instructions having the steps of identifying a clinical trial target reflecting a goal of the clinical trial, determining desired evaluability data categories to be gathered pertaining to a participant in the clinical trial, wherein an evaluability data of at least one of the evaluability data categories is used to determine the desirability of retaining the participant in the trial or incorporating the participant in at least one result of the clinical trial.

A further embodiment of the invention provides a medium suitable for use in an electronic device and having instructions for execution on the electronic device, the instructions having the steps of providing at least one of the group of historical subject compliance data and historical protocol data and generating at least one preferred compliance threshold by quantitative analysis of at least one of the group of the historical subject compliance data and the historical protocol data.

A further embodiment of the invention provides a medium suitable for use in an electronic device and having instructions for execution on the electronic device, the instructions having the steps of providing historical subject compliance data, generating at least one algorithm reflective of the historical subject compliance data by quantitative analysis of the historical subject compliance data, translating the at least one algorithm into at least one decision rule for analyzing subject compliance information and obtaining the subject compliance information. The steps further include comparing the subject compliance information to the at least one decision rule to determine if corrective action is needed and prompting corrective action if the step of comparing indicates that corrective action is needed.

Another embodiment of the invention provides a medium suitable for use in an electronic device and having instructions for execution on the electronic device, the instructions having the steps of providing historical subject compliance data and historical protocol data, generating a spectrum of compliance representative of the historical subject compliance data not compliant with the historical protocol data by quantitative analysis of the historical subject compliance data and the historical protocol data, obtaining subject compliance information, comparing the spectrum of compliance to the subject compliance information to determine if corrective action is needed and prompting corrective action if the step of comparing indicates that corrective action is needed.

A further embodiment of the invention provides a medium suitable for use in an electronic device and having instructions for execution on the electronic device, the instructions having the steps of providing historical subject compliance data, generating at least one predictive algorithm for predicting subject noncompliance by quantitative analysis of the historical subject compliance data, translating the at least one predictive algorithm into at least one prediction rule, obtaining subject compliance information, comparing the subject compliance information to the at least one prediction rule to determine if action is needed and prompting action if the step of comparing indicates that action is needed.

A further embodiment of the invention provides a medium suitable for use in an electronic device and having instructions for execution on the electronic device, the instructions having the steps of providing historical subject compliance data, generating at least one algorithm by quantitative analysis of the historical subject compliance data, translating the at least one algorithm into at least one decision rule and obtaining subject compliance information and comparing the subject compliance information to the at least one decision rule to determine if affirmative action is warranted.

A further embodiment of the invention provides a medium suitable for use in an electronic device and having instructions for execution on the electronic device, the instructions having the steps of displaying information to the participant and prompting input from the participant, accepting the input from the participant and decreasing an amount of prompting of the input from the participant upon an upon an automated determination that the participant has reported a predetermined number of events other than in response to the prompting by the portable electronic device.

BRIEF DESCRIPTION OF THE DRAWINGS

The foregoing and other objects, features and advantages of the invention will be apparent from the following description and apparent from the accompanying drawings.

DETAILED DESCRIPTION OF THE INVENTION

Figure 1:
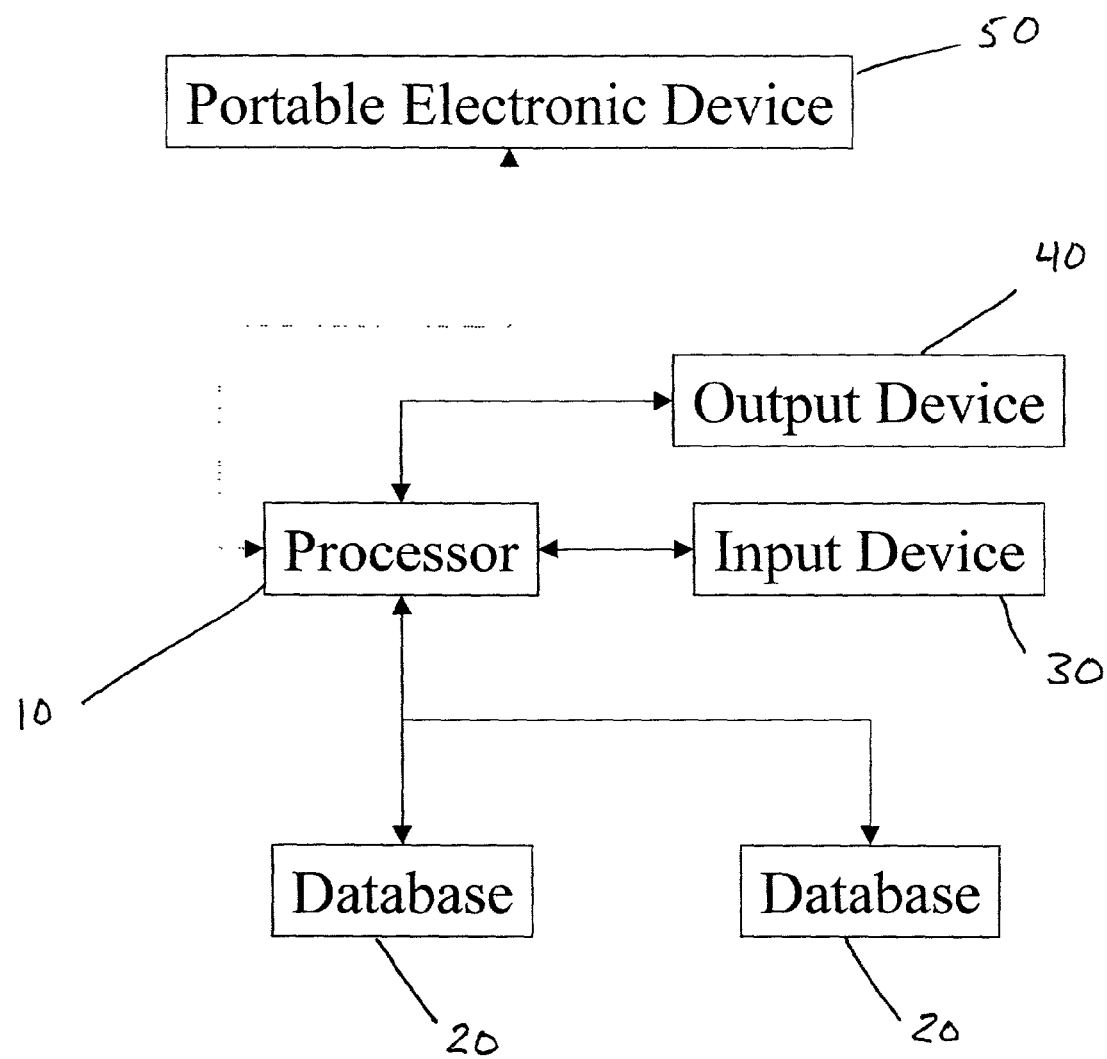
FIG. 1 illustrates a system according to an embodiment of the present invention.

The illustrative embodiment of the present invention is designed to develop research protocols for clinical trials, track and enhance subject compliance with protocol requirements and provide evaluability data related to subject performance in the clinical trial.

The illustrative embodiment involves an empirically derived set of algorithms and decision rules to predict, track and enhance subject compliance with research protocols. The illustrative embodiment uses algorithms and decision rules to provide an empirical approach for analysis of different types of subject noncompliance with research protocols. This actuarial approach to predicting and managing subject noncompliance with clinical trial protocols is consistent with empirical research demonstrating the superiority of actuarial prediction of human behavior as compared to subjective clinical judgment. According to an alternative embodiment of the invention, a portable electronic device is used to query and collect data from the subject.

As used herein "clinical trial" refers to a broad range of data collecting activities, including studies directed to monitoring of one or more conditions within a clinical trial group of subjects. One such example includes drug trials involving humans. As used herein "subject" refers to any participant in a clinical trial, whether or not the subject has any relationship to a doctor or other medical professional.

Data "evaluability" refers to the usefulness of the data for the intended clinical trial purpose. Various factors may affect data evaluability, principally the circumstances under which the data was collected and how closely the circumstances with the research protocol for the specific clinical trial.

"Trial data" or "clinical trial data" refers to data gathered for the principle purpose of the clinical trial. For example, trial data would include pain levels experienced by subjects in a pain medication clinical trial or craving levels in an anti-smoking medication clinical trial.

"Evaluability data" or "compliance data" or "compliance information" is data that relates to the circumstances under which the trial data was collected or other data pertaining to characteristics of the trial data or other evaluability data. Some examples include timeliness, consistency with other collected data, proximity of the data to an expected data range and completeness of the data.

"Historical protocol data" includes data specifying the research protocol of earlier clinical trials. Examples of historical protocol data can include questions posed to subjects, frequency of prompting of a subject during various times of the day or week, time allowed for subjects to respond to questions, requirements of subject behavior, and conditions mandating removal of a subject from specific analyses or from participation in the clinical trial.

As used herein "portable electronic device" refers to any electronic device that can be adapted for use by a subject and/or clinical staff for viewing and/or inputting information. Preferably, the portable electronic device will also have a visual, audible or tactile alarm to gain the attention of the subject. For example, a pager having a vibration alarm may be used as a portable electronic device. Further examples include, pagers with audible alarms and/or text messaging capabilities, a laptop computer or a cell phone. Preferably, according to the invention, a portable electronic device will be a handheld computer provided with a display and a data input feature, such as a touch-sensitive screen, or buttons to enable a subject to respond to questions posed on the display or to input unsolicited information. Examples of such portable electronic devices include the Palm Pilot by Palm, Inc or Windows-based devices running Pocket PC from Microsoft Corporation. Preferably, the portable electronic device will also be adapted to communicate with at least one other computer via a wireless connection or via a wired connection, including the use of a modem and/or a network, such as a LAN or the Internet.

According to an embodiment of the present invention, a system is provided as shown in FIG. 1. A processor 10 is provided and is adapted to communicate with at least one database 20. As discussed below, the database preferably stores data related to subject compliance and associated research protocols. An input device 30 is also provided to allow the subject or another person to provide input to the processor 10. The input device 30 may be a keyboard, a modem or other such device adapted for communication with the processor. An output device 40 is also preferably provided to receive and display information from the processor 10. Examples of output devices 40 include a printer and a monitor.

In one embodiment of the invention, a portable electronic device 50 is provided and selectively operatively coupled to the processor 10. The portable electronic device 50 can also include a processor and may serve as an alarm, an input device, an output device, and/or a database.

In one embodiment, the present invention includes software that resides on a portable electronic device. Preferably, the portable electronic device is a handheld portable computer.

In another embodiment, the present invention includes software that resides on a server. Optionally, the server may communicate with a computer or portable electronic device.

Figure 2:
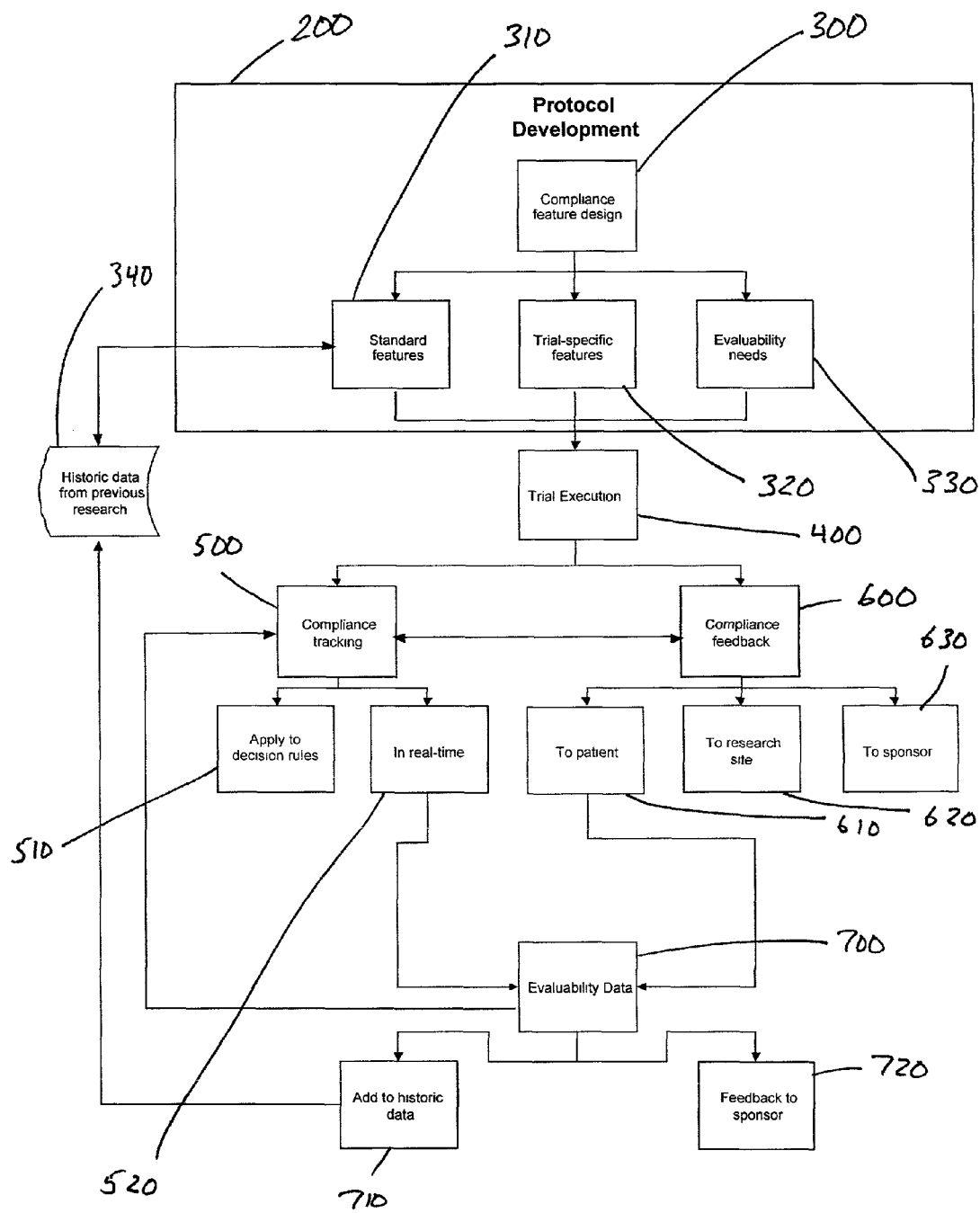
FIG. 2 provides a functional layout of one embodiment of the present invention.

FIG. 2 provides a functional layout of an embodiment of the present invention. Protocol development 200 involves a review of the goals of the clinical trial to determine research protocol including subject compliance targets prior to the start of the clinical trial. Preferably, compliance targets are developed in accordance with the invention disclosed in the co-pending patent application titled "Apparatus and Method for Prediction and Management of Subject Compliance in Clinical Research", U.S. patent application Ser. No. 09/825,534, now U.S. Pat. No. 6,879,970. Optionally, protocol development 200 can involve analysis of and updates to the protocol while the clinical trial is underway. Therefore, in accordance with an optional embodiment of the present invention, protocol development 200 can occur during trial execution 400.

The present invention preferably involves identification of compliance targets relevant to specific features of the research protocol prior to the start of the clinical trial. These compliance targets can then be used to track subject compliance. Once these compliance targets have been identified, compliance-enhancing features can optionally be developed for a specific clinical trial and can preferably be incorporated into the functionality of the portable electronic device.

It is also within the scope of the present invention to use empirically derived algorithms to determine the best compliance targets for a specific clinical trial by the use of the quantitative analysis methods of the patent application titled "Apparatus and Method for Prediction and Management of Subject Compliance in Clinical Research", U.S. patent application Ser. No. 09/825,534, now U.S. Pat. No. 6,879,970.

These algorithms could identify non-intuitive, combinations of variables derived from historical data from previous clinical trials. Combinations of different compliance targets identified from other clinical trials could be used to predict a set of variables to be tracked in order to maximize an ability to detect subject noncompliance. Preferably, algorithms are translated to decision rules to ease detection of subject noncompliance.

Examples of various types of data that may be collected according to an embodiment of the invention include variables that may represent 'non-intuitive' predictors such as: gender of the subject, disease severity, the time of the year, and the day of the week.

Protocol development 200 preferably includes compliance feature design 300 to incorporate features into the research protocol to enhance subject performance in complying with the research protocol. Compliance features are preferably active during the execution of the clinical trial. Compliance features may be provided by a portable electronic device driving the protocol for subjects by guiding the subject through the protocol, not requiring the subject to remember the details of all the research protocol. For example, the portable electronic device can activate an alarm to prompt the subject to view the device. The portable electronic device can then prompt the subject to answer appropriate questions to gather information as specified by the research protocol. Optionally, the portable electronic device can modify and tailor questions based on information provided by the subject or based on input from the clinical staff. Preferably, each subject is provided with a portable electronic device and will keep the portable electronic device in their possession at all times during the clinical trial.

By the use of the portable electronic device, the present invention also allows subjects to administer self-reports of trial data including subjective reports, such as pain reduction, objective symptom reporting, such as bowel movement or asthmatic episode and cognitive measures, such as arithmetic tasks or reaction time. The electronic device may also optionally be configured to synchronize with any portable physiological measurement device to gather data from, or communicate with, the physiological device.

Moreover, portable electronic devices can optionally track all aspects of their use, resulting in a comprehensive record of subject compliance with the research protocol. A preferred embodiment of the invention allows clinical trial staff to systematically collect data regarding subject compliance by tracking a variety of different components of compliance, as well as check in compliance against empirically derived algorithms and decision rules of compliance. These empirically derived algorithms and decision rules allow the disclosed invention to examine the data for nonintuitive and complex combinations of predictors to proactively determine whether the observed pattern of interaction with the portable electronic device suggests noncompliance. The patent application titled "Apparatus and Method for Prediction and Management of Subject Compliance in Clinical Research", U.S. patent application Ser. No. 09/825,534, now U.S. Pat. No. 6,879,970, provides additional detail regarding such algorithms and decision rules.

The portable electronic device also preferably conducts ongoing compliance checks and gives the subject feedback about their performance. For example logical psychometric or other inconsistencies can be determined by the portable electronic device. Actions of the portable electronic device are preferably processed according to decision rules. The portable electronic device can also vary its behavior based on the subject's behavior. For example, prompt frequency may be delayed or increased, or louder prompts may be provided. Also, vibration or visual alerts can be generated. Evaluability data related to the activity conducted with a portable electronic device is preferably transferred from the portable electronic device to a database for collecting information from multiple portable electronic devices. Such a database is preferably, a database hosted at a central location. In one embodiment of the invention, the database is hosted on PC-based server software and is preferably adapted for communication with other computers. Additional compliance checks are preferably performed on the server and feedback is given to subjects by clinical trial staff; the feedback could be face-to-face or remote. Finally, the evaluability data is used to determine the evaluability of subject data, and screen out subjects or parts of subjects' data during the data analysis and reporting of the clinical trial data or results. Thus, the present invention is preferably utilized from beginning to end of a clinical trial.

Compliance feature design 300 includes standard features 310, trial specific features 320, and evaluability needs 330. Incorporating standard features 310 within the research protocol preferably involves review of historic data from previous research 340, including prior operations of the invention on earlier clinical trials and other sources of data involving subject compliance and, preferably, associated research protocols. Preferably, standard features 310 incorporated into the protocol will be derived in accordance with co-pending patent application titled "Apparatus and Method for Prediction and Management of Subject Compliance in Clinical Research", U.S. patent application Ser. No. 09/825,534, now U.S. Pat. No. 6,879,970, and will involve historic data from related clinical trials. For example, a clinical trial related to a cardiovascular condition will preferably develop standard compliance features 310 from historic data involving cardiovascular clinical trials.

Many types of compliance enhancing features are possible. For example, to enhance subject compliance with regular monitoring of symptom severity, varying alarm tones could be used to engender compliance. For example, if subjects are prompted using an audible 'beep' to complete a symptom report, the tone may increase in volume and/or pitch to increase the probability that subjects will complete the report. Other examples of compliance-enhancing features include allowing subjects to delay a report if they are busy. Subjects can also initiate a brief suspension of monitoring if their activity precludes completion of a report, for example, while driving. The portable electronic device could automatically re-initiate monitoring after a set amount of time has elapsed, or alternatively the subject could re-initiate monitoring. These examples do not represent an exhaustive list of compliance enhancing features of the present invention.

According to a preferred embodiment of the present invention, the following data is gathered by the use of a portable electronic device: the number of completed assessments or the ratio to expected assessments; the number or percent of prompts from the portable electronic device for data input that were not replied to by the subject; a variety of time based variables, such as for example, a sleep/wake cycle, obtained by having the portable electronic device record when subjects went to sleep and awoke each day of the clinical trial; the amount of time a subject puts the portable electronic device in a suspend mode that temporarily prevents the diary from prompting the subject for a reply; how often and for how long subjects respond to a prompt by requesting the portable electronic device delay a reply period; the frequency with which a subject abandons the portable electronic device, for example, how often does the subject's pattern of inactivity with the portable electronic device suggest he/she has ceased complying with the research protocol.

Trial specific features 320 may also be included in compliance feature design 300 and may include specific aspects related to the current clinical trial. For example, compliance targets can also be identified based on specific characteristics of the disease state or clinical judgment of the clinical staff. For example, if subjects typically report a certain number of disease episodes per day, the present invention may target episodes per day as one variable to be tracked during the clinical trial and will automatically prompt subjects if a disease episode is not reported every 5 hours.

Evaluability needs 330 may also be incorporated in compliance feature design 300 and may involve tailoring compliance features in order to maximize evaluability data or address specific sponsor requirements. Preferably, evaluability needs 330 will be an integral part of the initial design of the research protocol. An example of an evaluability need 330 is a requirement that subject must report at least 5 disease episodes per day to be included in a particular analysis. In this example, how many disease episodes reports each day may be identified as an important variable to be tracked during trial execution.

During and/or after trial execution 400, compliance tracking 500 is performed and involves analyzing subject behavior data and comparing it to the research protocol. Compliance tracking data, e.g. evaluability data, is gathered during the clinical trial and compared to historic norms 510 during or after the clinical by the use of decision rules. Additional detail is provided in the patent application titled "Apparatus and Method for Prediction and Management of Subject Compliance in Clinical Research", U.S. patent application Ser. No. 09/825,534, now U.S. Pat. No. 6,879,970.

According to a further embodiment of the invention, algorithms can be used with decision rules to automatically generate feedback to both subjects and research staff. For example, an algorithm predicting a pattern of intermittent noncompliance with one facet of a clinical trial protocol could trigger a prompt to the subject on the portable electronic device to remain vigilant. Feedback could also be generated to the research staff to address an issue with the subject. Because the algorithms and decisions are preferably based on formal, empirical, and quantitative criteria, subjectivity can be removed from these decisions, which in turn minimizes the potential for bias.

An embodiment of the present invention preferably tracks compliance with the research protocol expected of subjects, such as timely completion of reports and compliance with the medication regimen. To successfully assess and remediate subject performance in clinical trials, the present embodiment preferably tracks compliance at several levels. If a portable electronic device is used for data entry, compliance may be tracked at the moment of data entry by determining whether or not the entry falls within acceptable parameters of the protocol. For example, is a response to a prompt required to be completed in the morning timely, or is the response delayed until the afternoon. Compliance tracking can also examine the content of the data entry itself to determine whether or not the subject is being compliant with the research protocol. For example: inconsistencies among two or more responses given; subject claiming they are in their living room and swimming. Compliance tracking can also take place over some span of time, such as for example, weekly, to examine patterns or rates of noncompliance over time. Compliance tracking can also be performed against data pertaining to the subject's behavior during the clinical trial. For example, trends in subject response times or in the responses themselves can be determined.

The present invention can optionally reduce the burden on a non-compliant subject in order to increase compliance rates by providing fewer prompts for information. Also, the present invention can reduce the number of prompts for a subject that has provided voluntary, unprompted information. In summary, the present invention can be interactive. The present invention is preferably configured to initially enhance compliance while evaluating compliance as the clinical trial progresses. Preferably, the present invention dynamically adjusts in response to the subject's behavior, in accordance with the decision rules.

Compliance feedback 600 may involve forwarding messages, activating alerts or taking some other action in order to provide information to the subject 610, the clinical trial staff, including the research site 620, or to the sponsor 630. Such messages may be include, for example positive feedback, corrective feedback or a recommendation to dismiss a subject from the clinical trial.

To increase the benefit of the compliance tracking feature of the present invention, compliance feedback is preferably provided to subjects, the research site, and the clinical trial sponsor in a timely fashion. Compliance tracking and compliance feedback may be conducted in an ongoing, timely manner on the portable electronic device itself. Compliance tracking and compliance feedback can occur also occur later, after data has been transmitted to a database, such as a database on a central server. In such a case, compliance feedback instructions can be sent back to the portable electronic device to provide feedback to subjects. Feedback for subjects can optionally be directed to clinical trial staff for delivery to the subjects.

According to an embodiment of the invention, a portable electronic device or a computer, such as a workstation or a server, can automatically check incoming data against a decision rule to determine if the pattern of responses require that a compliance alarm be triggered. Optionally, other demographic variables can also be checked by a decision rule. If one or more decision rules note that a problematic pattern of noncompliance or potential noncompliance is being observed, a number of actions may be taken. Examples of such actions include: posting a message on a website to be reviewed by the sponsor or research site, sending an e-mail or other type of notification, such as an automated call, to the subjects or research site coordinator, instructing the portable electronic device to display a certain message to the subject, instructing the portable electronic device to call the site during the subject's next interaction with the device, etc. These checks can either be triggered manually or automatically upon receipt of the data from the field.

According to an embodiment of the invention, the computer can perform the compliance analyses of incoming data instead of the compliance analyses being conducted by the portable electronic device. For example, the computer can analyze incoming data and compute the ratio of missed to completed assessments. This would be appropriate if the method of collection of the data did not otherwise allow the compliance data to be generated. For example, such a method of collection may involve written forms or an instrumented device not capable of computations.

According to another embodiment of the invention, the computer can execute more extensive compliance analyses than are capable on a portable electronic device. For example, more memory or processing power may be required to use the item response theory to examine the probability that a series of responses are likely as compared to an existing database of population norms for a given measure.

According to a further embodiment of the invention, the computer can aggregate a series of assessment data over time within or between subjects. These aggregated compliance analyses on the computer allow for greater capacity than may be capable on a portable electronic device.

According to an embodiment of the invention, the computer can provide data to be displayed. Data may be displayed at the computer itself or be transmitted to another location, such as via hardwired or wireless access to the computer, including a LAN or the Internet. The data can be processed to provide a graphical display to interested parties. Examples of those who may be interested in viewing the graphical representation of the compliance data include a site coordinator (who may be interacting with the subject), a clinical research organization (who may be responsible for study execution across a number of research locations), other agencies interested in the collection of the data, or the sponsor of the research.

According to another embodiment of the invention, the computer can provide ongoing aggregation of data across subjects to speed the time required to combine, clean, and make available final data.

The various features of the computer, such as a workstation or server, of the above embodiments of the invention may be used individually or in combination.

Subject changes in behavior in response to compliance feedback may also be assessed. That is, an embodiment of the present invention may assess subjects' behavior in response to feedback regarding their compliance with the research protocol. For example, the software can detect whether or not subjects have begun to follow the research protocol more closely as a function of having received previous feedback about their noncompliance with the protocol.

Compliance feedback can take many forms. Compliance feedback can be given to a subject at varying intervals at any location, ranging from frequent, timely feedback, to more episodic feedback based on aggregate measures of compliance. Systematic compliance feedback may be given to subjects to encourage continued compliance, remediate poor compliance, or administer rewards to subjects for their performance.

Compliance feedback may be given to the clinical trial staff. To maximize the impact of the compliance system on trial success, clinical trial staff preferably receives training in the monitoring and correcting of subject compliance according to the present invention.

In one embodiment, the present invention creates customized graphical summaries of compliance tracking data and produces standardized reports for delivery of compliance feedback to subjects, the research site and/or clinical trail staff. Research sites are instructed on how to give standardized feedback to subjects in order to remediate poor subject compliance.

The aggregation of this compliance feedback can optionally be compiled into subject and clinical trial status reports during the clinical trial. These reports are for the research site and/or sponsors, to be used in evaluating the progress of the clinical trial. These reports contain a summary of subjects' compliance with research protocol, and therefore are an indicator of data evaluability.

Compliance tracking data is timely 520 forwarded as it is collected to an evaluability database 700. Aggregation of compliance data enhances evaluation of subjects, prompting methodologies and research sites. Aggregated compliance data also allows for subjects to be examined for evaluability analyses. Also, evaluability data may be incorporated in compliance tracking 500 decisions during the course of a clinical trial. The evaluability database 700 also can provide additional historic data 710 to be included in a historic data database 340 upon which further research protocols are developed, as appropriate. The evaluability database 700 is also preferably made available to clinical staff and research sponsors. By making the evaluability database 700 accessible to clinical trial sponsors, sponsors are able to participate in decision making regarding the management of the clinical trial as the clinical trial is conducted. Furthermore, sponsors are able to monitor the progress of a clinical trial as it proceeds.

Evaluability data can be gathered in an evaluability database: a database that contains information relevant to the evaluability or acceptability of data from each subject. Evaluability data represents data that is of significant benefit for clinical trial sponsors. The evaluability database allows clinical trial sponsors to have timely evaluability data regarding the quality and consistency of the trial data. An example of trial data is efficacy data on the impact of the drug or medical device on the subject. In other words, the evaluability data allows clinical trial sponsors to have data about the quality of the trial data.

One specific use of the evaluability database is to determine whether or not a specific subject's data would be used in an analysis. For example, an analysis may be limited to those subjects who met minimal criteria for compliance. Another specific use of the evaluability database is to determine desirable trial data for a specific subject or among multiple subjects. This use of evaluability data involves whether or not specific data points within one or more subjects' trial data would be used in an analysis. For example, among all subjects, only trial data from days when compliance met acceptance criteria may be desired. In each instance, the evaluability data becomes an important and unique source of information regarding trial data quality in a clinical trial.

Evaluability data can be aggregated to create global, as well as disease and population-specific databases. The result of this aggregation of evaluability data provides an ability to predict subject noncompliance in clinical trials. This prediction ability increases as more evaluability data is available.

Evaluability data may also be reviewed by clinical trial staff. The periodicity of the data review could range from weekly to instantaneous, optionally using wireless technology or a web site located on the Internet. During the data review, the data can be checked using algorithms or decision rules to determine whether the pattern of subject behavior up to that point in the clinical trial triggers a decision rule, which may therefore recommend a course of action. Courses of action may include, for example providing feedback to the subject, the research site, the sponsor and/or the clinical trial staff. The review may examine data over varying time intervals to determine whether some type of corrective action is necessary. By the use of the present invention, evaluability data can be reviewed for critical patterns of factors related to noncompliance or other events, such as effectiveness of compliance enhancement measures, ranging from within-day assessments to patterns extending over many months of monitoring.

The portable electronic device is also preferably adapted to communicate with another computer to allow the clinical staff to consolidate the data from all subjects in the clinical trial into one location for review or processing. Preferably, the portable electronic device will also be adapted to communicate with at least one other computer via a wireless connection or via a wired connection, including the use of a modem and/or a network, such as a LAN or the Internet. For example, by the use of the Internet or a dial-up modem connection, a subject may submit information from the portable electronic device to the clinical staff from the subject's home.

In another embodiment, a portable electronic device or a computer is adapted to communicate with clinical trial equipment used for measuring, monitoring, controlling or recording data or a process of the clinical trial. Examples of such processes include administration of medication or monitoring of heart rates. The portable electronic device or a computer preferably automatically records desired data for incorporation in the clinical trial data or compliance data. A further example of clinical trial equipment is an instrumented bottle cap, which is capable of recording and/or reporting when a bottle is opened or closed.

In another embodiment, clock synchronization can be used to synchronize data from clinical trial equipment used for measuring, monitoring, controlling or recording data or a process of the clinical trial with data collected by a computer or portable electronic device for later analysis.

In another embodiment of the invention, a paper form, such as a case report form, can be used by the subject to record data. The data can then be entered into a database by the use of a portable electronic device or other computer at an appropriate time. Examples of case report forms include hand-written forms and forms that allow for machine readable marks to be made, enabling automated scanning of the case report forms during entry of the data into a computer.

In an alternative embodiment of the present invention, the methods of the present invention may be incorporated in instructions recorded on a medium suitable for use in an electronic device, such as a computer, computer network server or a portable electronic device. The medium can include, for example, a hard disk, RAM medium, diskette, CD-ROM or other optical or magnetic storage medium. The instructions can optionally be stored on a server that can be remote from the subject and/or clinical staff member.

Figure 3:
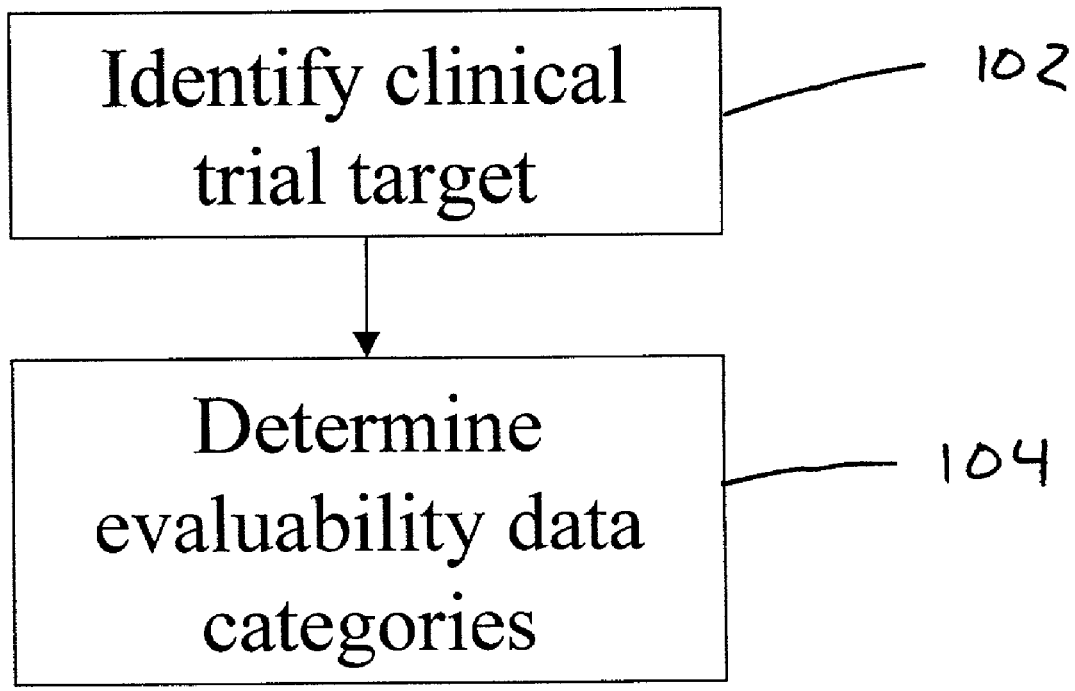
FIG. 3 illustrates a method according to an embodiment of the present invention.

According to a further embodiment of the invention, a flow chart illustrating a method of protocol development of the present invention is set forth in FIG. 3. First, a clinical trial target reflecting a goal of the clinical trial is identified, step 102. Next, desired evaluability data categories to be collected during the clinical trial are determined, step 104. Preferably, the desired evaluability data categories pertain to a participant in the clinical trial. Preferably, at least one of the evaluability data categories is used to determine the desirability of retaining the participant in the trial or incorporating the participant in the trial results.

Figure 4:
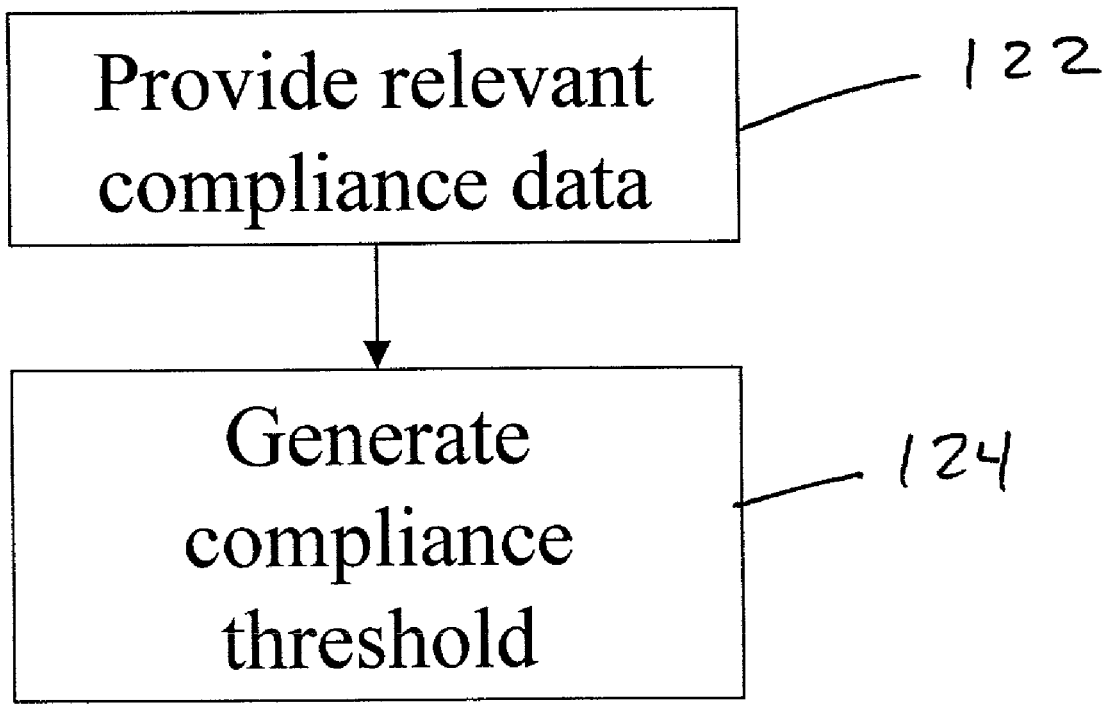
FIG. 4 illustrates a method according to an embodiment of the present invention.

According to another embodiment of the invention, a method for determining preferred targets for subject compliance is illustrated in FIG. 4. First, historical subject compliance data and historical protocol data are provided, step 122. Next, at least one preferred compliance threshold is generated, step 124. The preferred compliance threshold is preferably generated by quantitative analysis of the historical subject compliance data and the historical protocol data.

Figure 5:
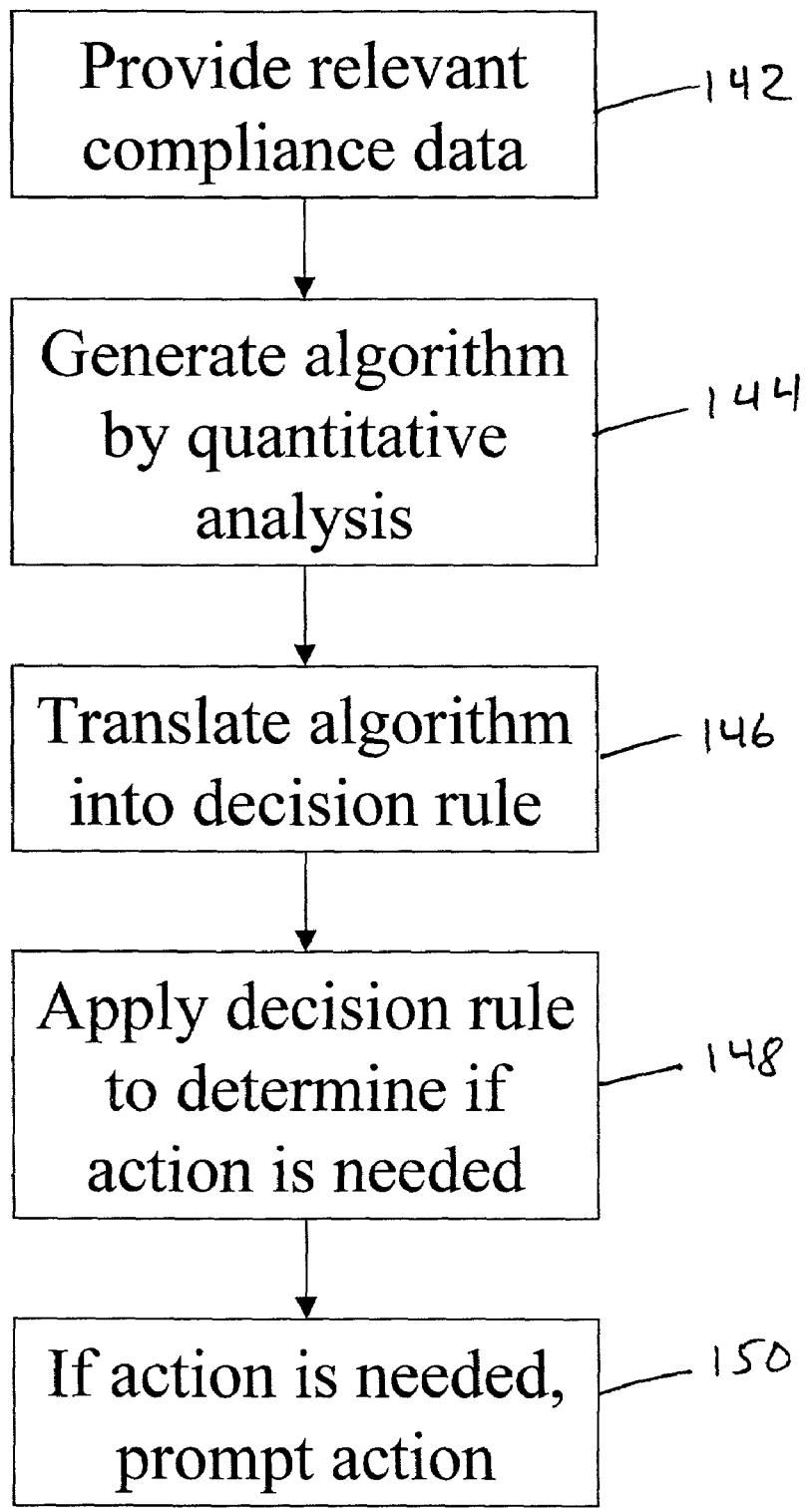
FIG. 5 illustrates a method according to an embodiment of the present invention.

According to a further embodiment of the invention, a flow chart illustrating a method of the present invention is set forth in FIG. 5. First, relevant subject compliance data, and associated protocol data, reflecting subject compliance with research protocols in clinical trials is provided, step 142. Subject compliance data and associated protocol data is preferably stored in one or more databases 20 and may be gathered from earlier clinical trials and/or earlier activities of a current clinical trial. Optionally, only subject compliance data may be stored, as some applications of the present invention may not require knowledge of associated historical protocol for use of the subject compliance data. For example, analysis of response times to questions may not require knowledge of the maximum permissible time for subjects to answer questions in earlier clinical trials. An output of the present invention preferably includes a database to provide subject compliance data and, preferably, associated protocol data, for later use by the invention.

Next, at least one algorithm representative of the subject compliance data is generated by quantitative analysis of the compliance data, step 144. Preferably, multiple algorithms are generated. The present invention involves the application of statistical and other quantitative methods to screen existing research data for markers of, e.g. variables related to, noncompliance with research protocols. Preferably, the subject compliance data is also reviewed to exclude invalid data. For example, data reported by one subject that appears to be well outside a range established by all other subjects can indicate invalid data.

Quantitative analysis methods are used to distinguish, identify, and predict instances of good and poor compliance. The quantitative analysis methods of the present invention may include, but are not limited to, application of a variety of statistical and data mining techniques, such as logistic regression, discriminant function analysis, classification and regression trees, neural networks, and multiple linear regression to screen existing data and derive algorithms to identify markers of noncompliance with research protocols.

Once the one or more algorithms of the invention have been derived from analysis of existing data, the algorithms can be translated into specific decision rules, step 146. Decision rules are essentially reformatted algorithms that can be applied to current subject compliance data to determine whether action is needed, step 148. Decision rules may determine a threshold of compliance or a threshold of noncompliance. Optionally, a decision rule may identify a spectrum of noncompliance, from minor noncompliance needing only corrective feedback, to significant noncompliance requiring subject removal from the clinical trial. Decision rules may be based on the specific dependent variable used to derive the algorithm or may be based on one or more differing variables.

Decision rules may be translated from algorithms that identify patterns of non-compliance data that are harbingers or leading indicators of later, more serious, non-compliance. This would allow early action to be taken based on these indicators. Such decision rules would typically be in the form of contingencies or conditions based on early compliance indicators.

Optionally, translation of algorithms to decision rules may involve human input or additional factors. For example, balancing the impact of a decision rule against the focus of the clinical trial may result in an alteration of the decision rule. For example, if subjects' heart rates are being monitored, frequency of prompting or loudness of reminder alerts may be minimized so as not to artificially raise subject heart rates. Also, clinical staff may alter decision rules based on their assessment of external factors outside of the scope of the quantitative analysis. An example may include providing more alerts to clinical staff instead of directly to subjects to provide more interaction between clinical staff and the subjects.

A decision rule may also be used to predict which subjects will fail to complete a clinical trial protocol. Therefore, a decision to rule to drop the subject from the clinical trial, or to work to improve subject performance, can be made at an early time. By providing those conducting a clinical trial with early feedback regarding subject noncompliance with a research protocol, the present invention improves clinical trial data quality and may potentially save both time and money by either improving the compliance of potentially noncompliant subjects or excluding unimprovable noncompliant subjects early in a clinical trial.

If action is determined to be needed, action is prompted, step 150. Examples of various actions include corrective action, compliance enhancing action, additional prompting of questions, reduced prompting of questions and sending an alert to the clinical staff to discuss an issue with the subject.

Additional detail regarding the method illustrated in FIG. 5 is provided in the patent application titled "Apparatus and Method for Prediction and Management of Subject Compliance in Clinical Research", U.S. patent application Ser. No. 09/825,534, now U.S. Pat. No. 6,879,970.

The present invention can yield very high rates of compliance with real-time, real world data collection by subjects. In one embodiment, the present invention for clinical trials (a) builds compliance features and checks into the software that drives the protocol, (b) tracks and optionally gives feedback regarding compliance during the trial, and (c) creates evaluability data that can be used to determine the evaluability of subjects at the end of the trial. Thus, this invention is a systematic methodology for timely, including immediate, data processing, summary, and feedback regarding subject performance in clinical trials.

These examples are meant to be illustrative and not limiting. The present invention has been described by way of example, and modifications and variations of the exemplary embodiments will suggest themselves to skilled artisans in this field without departing from the spirit of the invention. Features and characteristics of the above-described embodiments may be used in combination. The preferred embodiments are merely illustrative and should not be considered restrictive in any way. The scope of the invention is to be measured by the appended claims, rather than the preceding description, and all variations and equivalents that fall within the range of the claims are intended to be embraced therein.

Having described the invention, what is claimed as new and protected by Letters Patent is:

1. A method of determining if action is needed regarding subject compliance during a current clinical trial, wherein said current clinical trial comprises a group of subjects participating in said current clinical trial, comprising the steps of:
providing data on timeliness of a data entry from a previous clinical trial and either a) historical subject compliance data from said previous clinical trial or b) historical protocol data from said previous clinical trial, wherein said historical subject compliance data comprise data on a ratio of completed assessments to expected assessments, data on a subject's compliance with a medication regimen, data on a disease episode, or data on a characteristic of a subject's disease state, and wherein said historical protocol data comprise a question posed to a subject, a frequency of prompting of a subject during a day or week, an amount of time allotted for a subject to respond to a question, or a condition mandating removal of a subject from data analysis or from participation in a clinical trial;
generating a preferred compliance threshold for use during said current clinical trial by quantitative analysis of said data on timeliness of a data entry from said previous clinical trial and either a) said historical subject compliance data from said previous clinical trial or b) said historical protocol data from said previous clinical trial; and
obtaining subject compliance information from a subject in said group of subjects participating in said current clinical trial comprising using a portable electronic device capable of displaying information and receiving and storing input from a user to obtain said subject compliance information from said subject in said group of subjects participating in said current clinical trial; and
comparing said subject compliance information from said subject in said group of subjects participating in said current clinical trial to said preferred compliance threshold to determine if said action is needed for said subject in said group of subjects participating in said current clinical trial, wherein said action comprises removing all or part of data from said subject in said group of subjects participating in said current clinical trial from data analysis, removing all or part of the data from said subject in said group of subjects participating in said current clinical trial from a report, removing said subject in said group of subjects participating in said current clinical trial from said current clinical trial, prompting said subject in said group of subjects participating in said current clinical trial to view said portable electronic device, alerting clinical staff to contact said subject in said group of subjects participating in said current clinical trial regarding compliance with said current clinical trial, providing compliance feedback to said subject in said group of subjects participating in said current clinical trial to encourage continued compliance with said current clinical trial, providing compliance feedback to said subject in said group of subjects participating in said current clinical trial to remediate poor compliance with said current clinical trial, providing a report on the compliance of said subject in said group of subjects participating in said current clinical trial to said clinical staff or a clinical trial sponsor, or training said clinical staff in the monitoring and correcting of subject compliance.

2. The method of claim 1, further comprising a step of prompting said action if the step of comparing indicates that said action is needed.

3. The method of claim 1, wherein said compliance threshold remains unchanged throughout said current clinical trial.

4. A method of prompting an action if subject noncompliance indicates said action is needed during a current clinical trial wherein said current clinical trial comprises a group of subjects participating in said current clinical trial, comprising the steps of:
providing data on timeliness of a data entry and historical subject compliance data from a previous clinical trial, wherein said historical subject compliance data comprise data on a ratio of completed assessments to expected assessments, data on a subject's compliance with a medication regimen, data on a disease episode, or data on a characteristic of a subject's disease state; generating a predictive algorithm for predicting subject noncompliance by quantitative analysis of said historical subject compliance data;
translating said predictive algorithm into at least one prediction rule for use during said current clinical trial;
obtaining subject compliance information from a subject in said group of subjects participating in said current clinical trial comprising using a portable electronic device capable of displaying information and receiving and storing input from a user to obtain said subject compliance information;
comparing said subject compliance information from said subject in said group of subjects participating in said current clinical trial to the at least one prediction rule to determine if said action is needed for said subject in said group of subjects participating in said current clinical trial; and prompting said action if the step of comparing indicates that said action is needed.

5. The method of claim 4, wherein said step of providing further comprises providing historical protocol data from said previous clinical trial and wherein said step of generating further comprises quantitative analysis of said historical protocol data, wherein said historical protocol data comprise a question posed to a subject, a frequency of prompting of a subject during a day or week, an amount of time allotted for a subject to respond to a question, or a condition mandating removal of a subject from data analysis or from participation in a clinical trial.

6. The method of claim 4, further comprising a step of creating an evaluability database adapted to store data related to subject compliance.

7. The method of claim 6, further comprising a step of providing access to said evaluability database to a sponsor to allow said sponsor to make a determination regarding said subject in said group of subjects participating in said current clinical trial based on data from said evaluability database.

8. The method of claim 6, wherein said evaluability database is tailored to a condition affecting said subject in said group of subjects participating in said current clinical trial.

9. The method of claim 4, wherein said step of providing employs at least one database containing said the historical subject compliance data.

10. The method of claim 4, wherein said prediction rule is generated without data from activities of said current clinical trial.

11. A method of determining if an action is needed regarding subject compliance during a current clinical trial, wherein said current clinical trial comprise a group of subjects participating in said current clinical trial, comprising the steps of:

providing data on timeliness of a data entry and historical subject compliance data from a previous clinical trial, wherein said historical subject compliance data comprises data on a ratio of completed assessments to expected assessments, data on a subject's compliance with a medication regimen, data on a disease episode, or data on a characteristic of a subject's disease state;

generating an algorithm by quantitative analysis of said data on timeliness of a data entry and said historical subject compliance data;

translating said algorithm into a decision rule for use during said current clinical trial;

obtaining subject compliance information from a subject in said group of subjects participating in said current clinical trial; and comparing said subject compliance information from said subject in said group of subjects participating in said current clinical trial to said decision rule on a portable electronic device or a computer to determine if said action is needed for said subject in said group of subjects participating in said current clinical trial, wherein said action comprises removing all or part of data from said subject in said group of subjects participating in said current clinical trial from data analysis, removing all or part of data from said subject in said group of subjects participating in said current clinical trial from a report, removing said subject in said group of subjects participating in said current clinical trial from said current clinical trial, prompting said subject in said group of subjects participating in said current clinical trial to view said portable electronic device, alerting clinical staff to contact said subject in said group of subjects participating in said current clinical trial regarding compliance with said current clinical trial, providing compliance feedback to said subject in said group of subjects participating in said current clinical trial to encourage continued compliance with said current clinical trial, providing compliance feedback to said subject in said group of subjects participating in said current clinical trial to remediate poor compliance with said current clinical trial, providing a report on compliance of said subject in said group of subjects participating in said current clinical trial to said clinical staff or a clinical trial sponsor, or training said clinical staff in monitoring and correcting of subject compliance.

12. The method of claim 11, wherein said step of providing further comprises providing historical protocol data from said previous clinical trial and wherein said step of generating further comprises quantitative analysis of said historical protocol data, wherein said historical protocol data comprise a question posed to a subject, a frequency of prompting of a subject during a day or week, an amount of time allotted for a subject to respond to a question, or a condition mandating removal of a subject from data analysis or from participation in a clinical trial.

13. The method of claim 11, further comprising prompting said action if the step of comparing indicates that said action is warranted.

14. The method of claim 1, wherein said action further comprises reducing a number of occurrences of said step of obtaining subject compliance information.

15. The method of claim 11, wherein said action further comprises increasing a number of occurrences of said step of obtaining said subject compliance information.

16. The method of claim 11, wherein said action further comprises giving a reward to said subject in said group of subjects participating in said current clinical trial.

17. The method of claim 11, wherein said step of obtaining comprises using a portable electronic device capable of displaying information and receiving and storing input from a user.

18. The method of claim 11, wherein said decision rule is generated without data from activities of said current clinical trial.

19. A computer readable medium suitable for use in an electronic device and having instructions recorded thereon for execution on said electronic device, said instructions comprising the steps of:

providing data on timeliness of a data entry from a previous clinical trial and either a) historical subject compliance data from said previous clinical trial or b) historical protocol data from said previous clinical trial, wherein said historical subject compliance data comprise data on a ratio of completed assessments to expected assessments, data on a subject's compliance with a medication regimen, data on a disease episode, or data on a characteristic of a subject's disease state, and wherein said historical protocol data comprise a question posed to a subject, a frequency of prompting of a subject during a day or week, an amount of time allotted for a subject to respond to a question, or a condition mandating removal of a subject from data analysis or from participation in a clinical trial; and generating a preferred compliance threshold for use during a current clinical trial by quantitative analysis of said data on timeliness of a data entry from said previous clinical trial and either a) said historical subject compliance data from said previous clinical trial or b) said historical protocol data from said previous clinical trial, wherein said current clinical trial comprises a group of subjects participating in said current clinical trial, obtaining subject compliance information from a subject in said group of subjects participating in said current clinical trial, comprising using a portable electronic device capable of displaying information and receiving and storing input from a user to obtain said subject compliance information from said subject in said group of subjects participating in said current clinical trial; and comparing subject compliance information from said subject in said group of subjects participating in said current clinical trial to said preferred compliance threshold to determine if an action is needed for said subject in said group of subjects participating in said current clinical trial, wherein said action comprises removing all or part of data from said subject in said group of subjects participating in said current clinical trial from data analysis, removing all or part of data from said subject in said group of subjects participating in said current clinical trial from a report, removing said subject in said group of subjects participating in said current clinical trial from said current clinical trial, prompting said subject in said group of subjects participating in said current clinical trial to view said portable electronic device, alerting clinical staff to contact said subject in said group of subjects participating in said current clinical trial regarding compliance with said current clinical trial, providing compliance feedback to said subject in said group of subjects participating in said current clinical trial to encourage continued compliance with said current clinical trial, providing compliance feedback to said subject in said group of subjects participating in said current clinical trial to remediate poor compliance with said current clinical trial, providing a report on compliance of said subject in said group of subjects participating in said current clinical trial to said clinical staff or a clinical trial sponsor, or training said clinical staff in monitoring and correcting of subject compliance.

20. The computer readable medium of claim 19, wherein said compliance threshold remains unchanged throughout said current clinical trial.

21. A computer readable medium suitable for use in an electronic device and having instructions recorded thereon for execution on said electronic device, said instructions comprising steps of:

providing data on timeliness of a data entry and historical subject compliance data from a previous clinical trial, wherein said historical subject compliance data comprise data on a ratio of completed assessments to expected assessments, data on a subject's compliance with a medication regimen, data on a disease episode, or data on a characteristic of a subject's disease state;

generating an algorithm reflective of said historical subject compliance data by quantitative analysis of said data on timeliness of a data entry and said historical subject compliance data;

translating said algorithm into at least one decision rule for analyzing subject compliance information during a current clinical trial, wherein said current clinical trial comprises a group of subjects participating in said current clinical trial;

obtaining said subject compliance information from a subject in said group of subjects participating in said current clinical trial;

comparing said subject compliance information from said subject in said group of subjects participating in said current clinical trial to said decision rule to determine if an action is needed for said subject in said group of subjects participating in said current clinical trial; and prompting said action if the step of comparing indicates that said action is needed for said subject in said group of subjects participating in said current clinical trial, wherein said action comprises removing all or part of data from said subject in said group of subjects participating in said current clinical trial from data analysis, removing all or part of data from said subject in said group of subjects participating in said current clinical trial from a report, removing said subject in said group of subjects participating in said current clinical trial from said current clinical trial, prompting said subject in said group of subjects participating in said current clinical trial to view said portable electronic device, alerting clinical staff to contact said subject in said group of subjects participating in said current clinical trial regarding compliance with said current clinical trial, providing compliance feedback to said subject in said group of subjects participating in said current clinical trial to encourage continued compliance with said current clinical trial, providing compliance feedback to said subject in said group of subjects participating in said current clinical trial to remediate poor compliance with said current clinical trial, providing a report on compliance of said subject in said group of subjects participating in said current clinical trial to said clinical staff or a clinical trial sponsor, or training said clinical staff in monitoring and correcting of subject compliance.

22. A computer readable medium suitable for use in an electronic device and having instructions recorded thereon for execution on said electronic device, said instructions comprising steps of:

providing data on timeliness of a data entry from said previous clinical trial and either a) historical subject compliance data from said previous clinical trial or b) historical protocol data from said previous clinical trial, wherein said historical subject compliance data comprise data on a ratio of completed assessments to expected assessments, data on a subject's compliance with a medication regimen, data on a disease episode, or data on a characteristic of a subject's disease state, and wherein said historical protocol data comprise a question posed to a subject, a frequency of prompting of a subject during a day or week, an amount of time allotted for a subject to respond to a question, or a condition mandating removal of a subject from data analysis or from participation in a clinical trial;

generating a spectrum of compliance representative of said historical subject compliance data or said historical protocol data by quantitative analysis of said data on timeliness of a data entry and said historical subject compliance data or said historical protocol data;

obtaining subject compliance information from a subject in a group of subjects participating in a current clinical trial, wherein said current clinical trial comprises said group of subjects participating in said current clinical trial;

comparing said subject compliance information from said subject in said group of subjects participating in said current clinical trial to said spectrum of compliance representative to determine if an action is needed for said subject in said group of subjects participating in said current clinical trial; and prompting said action if said step of comparing indicates that said action is needed for said subject in said group of subjects participating in said current clinical trial, wherein said action comprises removing all or part of data from said subject in said group of subjects participating in said current clinical trial from data analysis, removing all or part of data from said subject in said group of subjects participating in said current clinical trial from a report, removing said subject in said group of subjects participating in said current clinical trial from said current clinical trial, prompting said subject in said group of subjects participating in said current clinical trial to view said portable electronic device, alerting clinical staff to contact said subject in said group of subjects participating in said current clinical trial regarding compliance with said current clinical trial, providing compliance feedback to said subject in said group of subjects participating in said current clinical trial to encourage continued compliance with said current clinical trial, providing compliance feedback to said subject in said group of subjects participating in said current clinical trial to remediate poor compliance with said current clinical trial, providing a report on compliance of said subject in said group of subjects participating in said current clinical trial to said clinical staff or a clinical trial sponsor, or training said clinical staff in monitoring and correcting of subject compliance.

23. A computer readable medium suitable for use in an electronic device and having instructions recorded thereon for execution on said electronic device, said instructions comprising steps of:
   providing data on timeliness of a data entry and historical subject compliance data from a previous clinical trial, wherein said historical subject compliance data comprise data on a ratio of completed assessments to expected assessments, data on a subject's compliance with a medication regimen, data on a disease episode, or data on a characteristic of a subject's disease state;
   generating a predictive algorithm for predicting subject noncompliance by quantitative analysis of said data on timeliness of a data entry and said historical subject compliance data;
   translating said predictive algorithm into at least one prediction rule for use during a current clinical trial;
   obtaining subject compliance information from a subject in a group of subjects participating in said current clinical trial wherein said current clinical trial comprises said group of subjects participating in said current clinical trial;
   comparing said subject compliance information from said subject in said group of subjects participating in said current clinical trial to said prediction rule to determine if an action is needed for said subject in said group of subjects participating in said current clinical trial; and
   prompting said action if said step of comparing indicates that said action is needed for said subject in said group of subjects participating in said current clinical trial, wherein said action comprises removing all or part of the data from said subject in said group of subjects participating in said current clinical trial from data analysis, removing all or part of the data from said subject in said group of subjects participating in said current clinical trial from a report, removing said subject in said group of subjects participating in said current clinical trial from said current clinical trial, prompting said subject in said group of subjects participating in said current clinical trial to view said portable electronic device, alerting clinical staff to contact said subject in said group of subjects participating in said current clinical trial regarding compliance with said current clinical trial, providing compliance feedback to said subject in said group of subjects participating in said current clinical trial to encourage continued compliance with said current clinical trial, providing compliance feedback to said subject in said group of subjects participating in said current clinical trial to remediate poor compliance with said current clinical trial, providing a report on compliance of said subject in said group of subjects participating in said current clinical trial to said clinical staff or a clinical trial sponsor, or training said clinical staff in monitoring and correcting of subject compliance.

24. A computer readable medium suitable for use in an electronic device and having instructions recorded thereon for execution on said electronic device for determining if an action is needed regarding subject compliance during a current clinical trial, wherein said current clinical trial comprises a group of subjects participating in said current clinical trial, said instructions comprising steps of:
   providing data on timeliness of a data entry and historical subject compliance data from a previous clinical trial, wherein said historical subject compliance data comprise data on a ratio of completed assessments to expected assessments, data on a subject's compliance with a medication regimen, data on a disease episode, or data on a characteristic of a subject's disease state;
   generating an algorithm by quantitative analysis of said data on timeliness of a data entry and said historical subject compliance data;
   translating said algorithm into at least one decision rule for use during said current clinical trial;
   obtaining subject compliance information from a subject in said group of subjects participating in said current clinical trial; and
   comparing said subject compliance information from said subject in said group of subjects participating in said current clinical trial to said decision rule to determine if said action is needed for said subject in said group of subjects participating in said current clinical trial, wherein said action comprises removing all or part of the data from said subject in said group of subjects participating in said current clinical trial from data analysis, removing all or part of the data from said subject in said group of subjects participating in said current clinical trial from a report, removing said subject in said group of subjects participating in said current clinical trial from said current clinical trial, prompting said subject in said group of subjects participating in said current clinical trial to view said portable electronic device, alerting clinical staff to contact said subject in said group of subjects participating in said current clinical trial regarding compliance with said current clinical trial, providing compliance feedback to said subject in said group of subjects participating in said current clinical trial to encourage continued compliance with said current clinical trial, providing compliance feedback to said subject in said group of subjects participating in said current clinical trial to remediate poor compliance with said current clinical trial, providing a report on compliance of said subject in said group of subjects participating in said current clinical trial to said clinical staff or a clinical trial sponsor, or training said clinical staff in monitoring and correcting of subject compliance.

25. The method of claim 1, wherein said step of providing comprises providing said historical protocol data, and wherein said step of generating further comprises quantitative analysis of said historical protocol data.

26. The method of claim 1, 4, or 11, wherein said step of generating employs multiple linear regression, discriminant function analysis, logistic regression, neural networks, classification trees or regression trees.

27. The method of claim 1 or 11, wherein said step of providing employs at least one database containing the historical subject compliance data.

28. The method of claim 1, 4, or 11, wherein said historical subject compliance data further comprise data on whether a subject had a relationship with a doctor or other medical professional, data on a number or percent of prompts not replied to by a subject, data on a subject's sleep/wake cycle, data on whether a subject had a bowel movement, data on an amount of time a portable electronic device is in suspend mode, data on a subject's gender, or data on a subject's location.

29. The method of claim 1, 4, or 11, wherein said action further comprises decreasing said portable electronic device's prompt frequency, increasing said portable electronic device's prompt frequency, or increasing the loudness of an audible prompt of said portable electronic device.

30. The method of claim 1, 4, or 11, wherein said action further comprises administering a reward to said subject in said group of subjects participating in said current clinical trial.

31. The computer readable medium of claim 19, 21, 22, 23, or 24, wherein said historical subject compliance data further comprise data on whether a subject had a relationship with a doctor or other medical professional, data on a number or percent of prompts not replied to by a subject, data on a subject's sleep/wake cycle, data on whether a subject had a bowel movement, data on an amount of time a portable electronic device is in suspend mode, data on a subject's gender, or data on a subject's location.

32. The computer readable medium of claim 19, 21, 22, 23, or 24, wherein said action further comprises decreasing said portable electronic device's prompt frequency, increasing said portable electronic device's prompt frequency, increasing the loudness of an audible prompt of said portable electronic device, or administering a reward to said subject in said group of subjects participating in said current clinical trial.

33. The computer readable medium of claim 23, wherein said prediction rule is generated without data from activities of said current clinical trial.

34. The computer readable medium of claim 21 or 24, wherein said decision rule is generated without data from activities of said current clinical trial.

* * * * *

UNITED STATES PATENT AND TRADEMARK OFFICE
CERTIFICATE OF CORRECTION

PATENT NO. : 8,065,180 B2  
APPLICATION NO. : 09/825533  
DATED : November 22, 2011  
INVENTOR(S) : Hufford et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1593 days.

Signed and Sealed this
Twenty-fourth Day of July, 2012

David J. Kappos
*Director of the United States Patent and Trademark Office*

UNITED STATES PATENT AND TRADEMARK OFFICE
CERTIFICATE OF CORRECTION

PATENT NO.        : 8,065,180 B2                                         Page 1 of 1
APPLICATION NO.   : 09/825533
DATED             : November 22, 2011
INVENTOR(S)       : Michael R. Hufford et al.

It is certified that error appears in the above-identified patent and that said Letters Patent is hereby corrected as shown below:

In the Claims

COLUMN 17, LINE 28, CLAIM 9:

"said the historical" should be --said historical--

Signed and Sealed this
Fourteenth Day of April, 2015

Michelle K. Lee
*Director of the United States Patent and Trademark Office*